Figure 1:
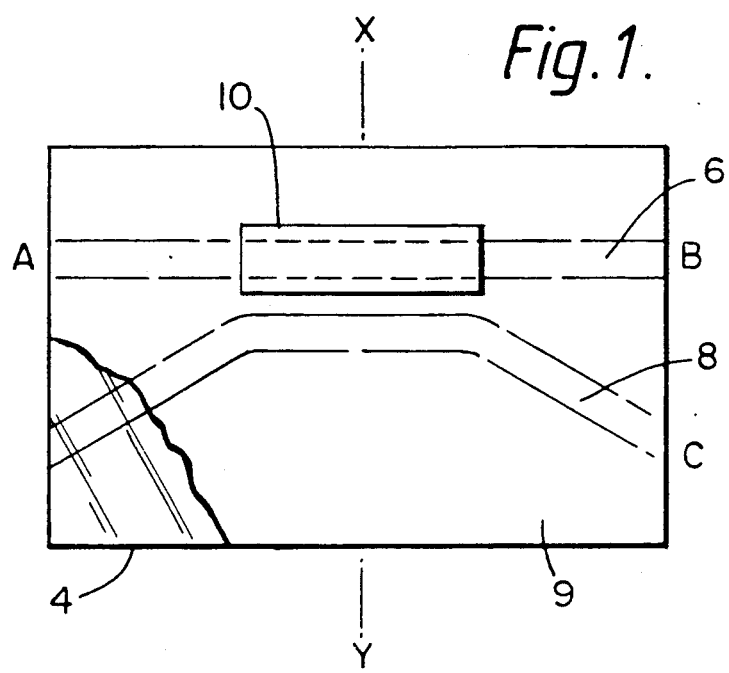

United States Patent [19]

Allen et al.

[11] Patent Number: 5,047,516
[45] Date of Patent: Sep. 10, 1991

[54] AZO COMPOUND SUITABLE FOR USE IN NON-LINEAR OPTICS

[75] Inventors: Simon Allen, Cheadle Hulme; Paul F. Gordon, Rochdale, both of England

[73] Assignee: Imperial Chemical Industries PLC, London, England

[21] Appl. No.: 190,672

[22] Filed: May 5, 1988

[30] Foreign Application Priority Data

May 5, 1987 [GB] United Kingdom ............... 8710572
Jul. 24, 1987 [GB] United Kingdom ............... 8717594

[51] Int. Cl.⁵ ............... C09B 29/01; C09B 29/085; G02F 1/13
[52] U.S. Cl. ............... 534/649; 534/581; 534/651; 534/728; 534/851; 534/852; 534/853
[58] Field of Search ............... 534/603, 649, 651, 851, 534/852, 853

[56] References Cited

U.S. PATENT DOCUMENTS

| 2,393,652 | 1/1940 | Olpin et al. | 534/649 X |
| 2,559,787 | 7/1951 | Olpin et al. | 534/853 X |
| 3,351,580 | 11/1967 | Koike et al. | 534/649 |
| 4,804,747 | 2/1989 | Allen et al. | 534/649 X |

FOREIGN PATENT DOCUMENTS

| 292139 | 11/1988 | European Pat. Off. | 534/651 |
| 293093 | 11/1988 | European Pat. Off. | 534/651 |
| 1544386 | 5/1969 | Fed. Rep. of Germany | 534/651 |
| 2204053 | 11/1988 | United Kingdom | 534/649 |

OTHER PUBLICATIONS

Inukai et al., Chemical Abstracts, vol. 106, No. 224617b (1987).
Osman et al., Chemical Abstracts, vol. 88, No. 97480j (1978).
Steinstraesser, Chemical Abstracts, vol. 76, No. 14080g (1972).

Primary Examiner—Mary C. Lee
Assistant Examiner—Fiona T. Powers
Attorney, Agent, or Firm—Cushman, Darby & Cushman

[57] ABSTRACT

An azo compound of the formula:

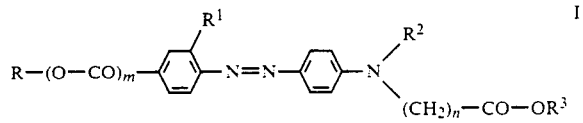

wherein
R is an non-hydrophilic aliphatic or cycloaliphatic group containing from 8 to 40 carbon atoms;
m is 0 or 1;
$R^1$ is $NO_2$, CN or $COOR^2$;
$R^2$ is H or $C_{1-4}$-alkyl;
n is from 1 to 4 and
$R^3$ is H, a metal or a group containing a tetravalent N atom.

The compound has non-linear optical properties which make it suitable for use in an optical element such as a waveguide, for altering the characteristics of light passing through the element.

7 Claims, 1 Drawing Sheet

AZO COMPOUND SUITABLE FOR USE IN NON-LINEAR OPTICS

This specification describes an invention relating to an azo compound and to the application thereof in non-linear optics (NLO).

According to the present invention there is provided an azo compound of the formula:

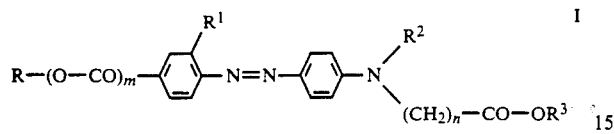

wherein
R is an non-hydrophilic aliphatic or cycloaliphatic group containing from 8 to 40 carbon atoms;
m is 0 or 1;
$R^1$ is $NO_2$, CN or $COOR^2$;
$R^2$ is H or $C_{1-4}$-alkyl;
n is from 1 to 4 and
$R^3$ is H, a metal or a group containing a tetravalent N atom.

By the term non-hydrophilic is meant that the group R should not carry hydrophilic substituents, such as carboxylate, sulphonate, phosphonate and hydroxyl.

It is preferred that R is a long chain aliphatic and/or cycloaliphatic group, preferably the former, containing from 8 to 20 and more preferably from 12 to 20 carbon atoms. Minor variations in chain length within these preferred limits have little effect on the non-linear optical properties of the compound. It is also preferred that the aliphatic chain is unbranched or, at most, contains only one or two branches, each containing one or two carbon atoms.

The long chain aliphatic or cycloaliphatic group represented by R is preferably alkyl, alkenyl or cycloalkyl or a group containing a mixture of these. The carbon chain in R may be interrupted by heteroatoms, especially oxygen or sulphur, but it is preferred that there is not more than one heteroatom for every twelve carbon atoms in the chain. The group represented by R may carry non-hydrophilic substituents, such as halogen atoms, but is preferably a hydrocarbon.

Examples of the group represented by R are octyl, nonyl, decyl, hendecyl, dodecyl (lauryl), tridecyl, tetradecyl (myristyl), pentadecyl, hexadecyl (cetyl), heptadecyl (margaryl), octadecyl (stearyl), nonadecyl, eicosanyl (archadiyl), heneicosanyl, docasanyl (behenyl), tricosanyl, tetracosanyl (lignoceryl), hexacosanyl (ceryl), 9-hexadecenyl (palmitoleyl), 9-octadecenyl (oleyl), 10-eicosenyl, 9,12-octadecadienyl (linoleyl) and 6-hexoxyhexyl.

It is preferred that m is 1.
It is preferred that $R^1$ represents a nitro group.
It is preferred that $R^2$ is H or methyl.
It is preferred that n is 1 or 2.

Where $R^3$ is a metal, it is preferably divalent. Preferred metals are cadmium, barium, lead and calcium and other suitable metals are manganese, zinc, magnesium and strontium.

Where $R^3$ is a group containing a tetravalent nitrogen atom this may be ammonium, such as $NH^4$, mono-, di- or tri-substituted or quaternary ammonium, bis(ammonium), such as alkylene- and alkenylene-diammonium, guanidinium, biguanidinium and amidinium. The tetravalent N atom may carry substituents other than hydrogen and suitable substituents include alkyl, such as methyl, ethyl, lauryl, cetyl, stearyl, aryl, such as phenyl, aralkyl, such as benzyl, cycloalkyl, such as cyclohexyl, which may themselves be substituted by such as $C_{1-4}$-alkyl, e.g. tolyl, $C_{1-4}$-alkoxy, e.g. anisyl and ethoxyethyl, halogen, e.g. chlorophenyl and hydroxy, e.g. hydroxyethyl. Specific examples of suitable groups are $NH_4$, $N(CH_3)_4$, $N(C_2H_4OH)_4$, $N(CH_3)_3(C_{18}H_{37})$, $H_3N-C_2H_4-NH_3$.

The compound of Formula I may be prepared by diazotising a substituted aniline of the formula:

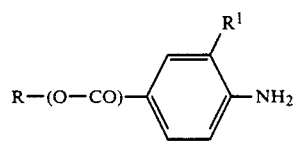

and coupling with with a N-substituted aniline of the formula:

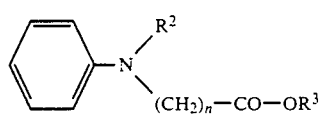

Preferred compounds of Formula I are those derived from a diazotisable aniline of Formula II in which R is $C_{12-18}$-alkyl and $R^1$ is nitro, especially 2-nitro-4-[dodecoxycarbonyl]aniline, 2-nitro-4-[heptadecoxycarbonyl]aniline, 2-nitro-4-[octadecoxycarbonyl]aniline and 2-nitro-4-dodecylaniline, and an N-substituted aniline of Formula III in which $R^2$ is methyl or ethyl, n is 2 and $R^3$ is H, Ca or Cd, especially N-methyl-N-(2-[hydroxycarbonyl]ethyl)aniline, N-ethyl-N-(2-[hydroxycarbonyl]-ethyl)aniline and N-(2-[hydroxycarbonyl]ethyl)aniline and the calcium and cadmium salts thereof. Specific examples of preferred compounds of Formula I are:

4-(2-nitro-4-[heptadecyloxycarbonyl]phenylazo)-N-methyl-N-(2-[hydroxycarbonyl]ethyl)aniline, 4-(2-nitro-4-[heptadecyloxycarbonyl]phenylazo)-N-ethyl-N-(2-[hydroxycarbonyl]ethyl)aniline, 4-(2-nitro-4-[heptadecyloxycarbonyl]phenylazo)-N-(2-[hydroxycarbonyl]ethyl)aniline, 4-(2-nitro-4-[dodecyloxycarbonyl]phenylazo)-N-methyl-N-(2-[hydroxycarbonyl]ethyl)aniline, 4-(2-nitro-4-[dodecyloxycarbonyl]phenylazo)-N-ethyl-N-(2-[hydroxycarbonyl]ethyl)aniline, 4-(2-nitro-4-[octadecyloxycarbonyl]phenylazo)-N-methyl-N-(2-[hydroxycarbonyl]ethyl)aniline 4-(2-nitro-4-[octadecyloxycarbonyl]phenylazo)-N-ethyl-N-(2-[hydroxycarbonyl]ethyl)aniline and 4-(2-nitro-4-dodecylphenylazo)-N-methyl-N-(2-[hydroxycarbonyl]ethylaniline and the calcium and cadmium salts thereof.

The compound of Formula I is non-centrosymmetric and substantially polarised along its longitudinal axis because the carboxyl, nitro and cyano groups are electron-withdrawing and the N-alkylcarboxylate group is electron-donating. A molecule of the compound can, thus, be represented as an electronic vector directed along this axis from the N-alkylcarboxylate group towards the aliphatic group, R.

It has been found that the compound of Formula I (hereinafter referred as the "present NLO compound") is adapted for the preparation of optical elements having non-linear optical properties which can effect changes in the properties of an optical signal.

According to a second feature of the present invention there is provided an optical element having non-linear optical properties comprising a transparent or reflecting substrate having at least a partial superficial coating comprising at least one monolayer of a compound of Formula I provided that, where there is more than one monolayer, the molecules in the layers are aligned in the same manner.

By "aligned in the same manner" is meant that the vectors along the longitudinal axes of the molecules are substantially parallel and in the same sense. Where the monolayers of the present NLO compound are adjacent, the N-alkylcarboxylate groups of the molecules in one monolayer will be adjacent to the aliphatic groups (R) in the adjacent monolayer ("head to tail" array).

It is, however, not essential that the monolayers of the present NLO compound are adjacent and it can be advantageous to separate the monolayers with intervening layers of other materials, especially those which assist the molecules of Formula I to adopt a head to tail array.

Where the substrate is transparent at the wavelength of light to be used it may be in the form of an optical waveguide on the outer surface of which the present NLO compound is deposited. With this form of element an optical signal passing along the waveguide interacts with the superficial coating of the present NLO compound, via the evanescent wave which extends into this coating, and gives rise to non-linear optical effects. Examples of suitable substances for a substrate in the form of a waveguide are glass, lithium niobate and silicon nitride on oxidised silicon.

Alternatively, a transparent substrate may be in the form of a plate or disc on one, or both, surfaces of which a coating of the present NLO compound can be formed in discrete monolayers. With this form of element a non-linear optical effect may be obtained by transverse illumination of the substrate and film(s). Suitable substrates for such an optical element include glass, silica and polymethylmethacrylate (PMMA).

Where the substrate is reflecting it conveniently has a plane reflecting surface on which a superficial coating of the present NLO compound, in discrete monolayers, may be formed so that the optical signal passes through the coating immediately before and after contact with the reflecting surface. Examples of suitable materials for the reflecting substrate are aluminium, silver, or aluminium or silver films deposited on a support substrate such as glass, silica, quartz or PMMA. With this form of optical element it is possible to attain efficient non-linear processes by exciting the so called "surface plasmon" modes reported in the literature [Stegman et al, Appl. Phys. Lett. 41 (10) 906, 1982; Sand et al, Appl. Optics 21 (22) 3993, 1982].

The optical element of the second aspect of the invention can be prepared by a Langmuir-Blodgett technique and according to a third aspect of the invention there is provided a method for the preparation of an optical element having non-linear optical properties which comprises passing a surface of a transparent or reflecting substrate into and out of a Langmuir trough containing a liquid carrying a superficial monomolecular layer of a compound of Formula I. Where the layers of the present NLO compound are not adjacent intervening layers may be formed by passing the substrate into the liquid through a surface carrying a superficial layer of the present NLO compound and out of the liquid through another surface carrying a superficial layer of a different compound, or vice versa.

The liquid, hereinafter referred to as the sub-phase, is preferably an aqueous medium and the mono-molecular layer or layers are obtained in the normal manner by adjustment of the surface area with movable dams.

The optical element of the second aspect of the invention in various forms, is capable of producing second order non-linear optical effects in a number of ways in various optical devices.

According to a fourth aspect of the present invention there is provided an optical device comprising a non-linear optical element in accordance with the second aspect of the present invention.

An optical device in accordance with the present invention, in which the optical element comprises a substrate in the form of a transparent waveguide having an intimate coating formed by multiple layers of the present NLO compound, consists of an oxidised silicon plate having a first superficial (lower) coating of silicon nitride to form a superficial plane waveguide and a second superficial (upper) coating comprising discrete monolayers of the present NLO compound. In operation, a first optical signal is passed through the waveguide, (in the plane of the waveguide) and interacts with the coating, by way of the evanescent wave which extends into the coating. This interaction generates a second optical signal, at the second harmonic frequency with respect to the first optical signal, which can be detected in the combined optical signal leaving the waveguide.

Figure 2:
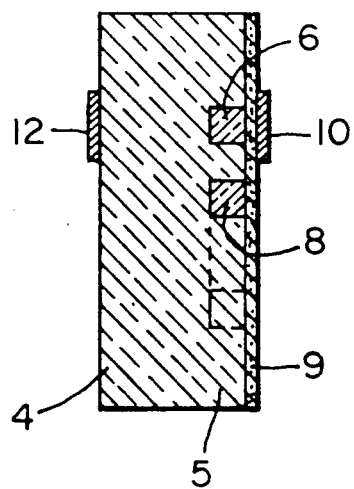

Another device in accordance with the present invention is described in relation to FIGS. 1 & 2 of the accompanying drawings, in which FIG. 1 is a plan view and FIG. 2 is a cross-section on the line X-Y in FIG. 1.

In the device the optical element comprises a glass substrate, 4, in the upper surface region, 5, of which are two transparent stripe waveguides, 6 & 8, formed in the desired pattern by the well-known ion exchange or ion bombardment techniques. The stripe waveguides are positioned to run closely parallel over the central part of their length during which they are separated by a distance of a few micrometers (typically 2–5 μm). The surface of the substrate, 4, is covered with a coating, 9, of discrete monolayers of the present NLO compound. A pair of electrodes, 10, 12, connected to a power source, not shown, is arranged with one electrode, 10, above and the other, 12, below one of the stripe waveguide, 6. In operation an optical signal is passed through the first waveguide, 6, from A to B and a voltage is applied across the electrodes. This alters the refractive index of the coating, due to the d.c. electro-optic (Pockels) effect, and thus the propagation constant of the first waveguide, 6. By suitable adjustment of the applied voltage the propagation constant of the first waveguide, 6, can be arranged so that the optical signal passing through this waveguide, 6, is coupled into the second waveguide, 8, and produces a second optical signal emerging from the device at C.

The optical element of the second aspect of the present invention may be used in other known forms of optical device incorporating an optical element by replacing the NLO compound used therein, e.g. lithium niobate, with the present NLO compound.

The invention is further illustrated by the following examples in which all parts and percentages are by weight unless otherwise indicated.

EXAMPLE 1

(a) 2-Nitro-4-(heptadecyloxycarbonyl)aniline

A mixture of 2-nitro-4-carboxyaniline (0.52 g), heptadecanol (0.7 g) and dimethylaminopyridine (20 mg) in dichloromethane (20 ml) was prepared and dicyclohexyldicarbodiimide (0.62 g) was added. The mixture was stirred for 48 hours and filtered. After separating between chloroform and 3% caustic soda solution the organic phase was washed with water, dried with magnesium sulphate and the solvent removed to leave a yellow solid. The solid was purified by chromatography to give a yellow solid which was recrystallised from 50:50 chloroform-hexane (yield: 0.85 g, m.p. 103°–105° C.).

(b) 4-(2-nitro-4-heptadecyloxycarbonylphenylazo)-N-methyl-N-(2-[hydroxycarbonyl]ethyl)aniline (NHMHA)

2-Nitro-4-(heptadecyloxycarbonyl)aniline (0.42 g) was added to cold nitrosyl-sulphuric acid (70 mg of sodium nitrite and 1.5 ml of 98% sulphuric acid) and stirred at 0°–5° C. for 1.5 hours. Urea (0.1 g) was added and then the resulting mixture was added to a cold solution of N-methyl-N-(2-hydroxycarbonylethyl)aniline in a 1:1 mixture of acetic and propionic acids (10 ml). Sodium acetate was added and the reaction mixture was stirred for 1 hour after which time it was diluted with water and filtered. The red solid was purified by chromatography to give red product (yield: 0.15 g; mass spec: M+, 610).

EXAMPLE 2

4-(2-nitro-4-dodecylphenylazo)-N-methyl-N-(2-[hydroxycarbonyl]ethyl)aniline (NDMHA)

2-Nitro-4-dodecylaniline (3.06 g) was dissolved in acetic acid (15 ml) and propionic acid (15 ml) and warmed whilst dilute hydrochloric acid (5 ml) was added. The mixture was cooled to 0° C. and sodium nitrite (0.7 g) was added at 0° C. The diazotised amine was then added to N-methyl-N-(2-hydroxycarbonylethyl)aniline (1.79 g) in water (100 ml) with dilute hydrochloric acid (3 ml). Sodium acetate was added until colour developed and the mixture was stirred for 0.5 hours. The crude product was recrystallised from $CH_2Cl_2$ to give a red solid (0.2 g).

EXAMPLE 3

A dipping bath was prepared by slowly dripping a 2.0 millimolar (mM) solution of NHMHA (as prepared in Example 1) in chloroform from a micro-syringe onto the surface of a sub-phase in a Joyce-Loebl Langmuir Trough. The sub-phase consisted of a 0.25 mM aqueous solution of calcium acetate in water at pH 6.3 (water purified using a Milli-Q system) The solvent was permitted to evaporate for a few minutes and the surface pressure was adjusted to 30 milli-Newtons/meter (mN/m) by movement of the barriers and maintained at this level throughout the dipping process.

A thin glass plate, pre-cleaned by ultrasonic washing in chloroform and methanol, was successively dipped into and withdrawn from the sub-phase at a rate of 0.5 cm/min. Deposition of a mono-molecular layer of NHMHA occurred substantially only during withdrawal of the plate from the sub-phase and dipping was continued until a thick coating comprising a plurality of mono-molecular layers of NHMHA had been built up on all surfaces of the plate which had passed into the sub-phase.

Substantially all the molecules of NHMHA in the coating were aligned in parallel array with their vectors in the same sense, i.e. the molecules in the separate monolayers were in "head to tail" array (Z-type deposition). The resulting optical element (hereinafter referred to as "OA1") comprised a glass substrate coated on both plane surfaces with a plurality of monolayers of NHMHA.

EXAMPLE 4

The procedure of Example 3 was repeated using NDMHA in place of NHMHA. The optical element produced is hereinafter referred to as OA2.

EXAMPLE 5

The optical element described in Example 3 (OA1) was used in the following manner to demonstrate the non-centro-symmetric nature of the applied film.

A beam of radiation from a Nd:YAG pulsed laser (wavelength: 1,064 nm; pulse duration 20 ns; repetition rate 10 Hz) was passed transversely through the plate and the film of CHNAB. The intensity of radiation at the second harmonic (wavelength: 530 nm) generated during passage through the element, after filtering out the transmitted radiation at the fundamental wavelength (1,064 nm), was detected and measured with a photomultiplier. After calibration with a 2 mm thick quartz reference plate, the calculated value of the second order NLO coefficient, Khi$^{(2)}$, was $6.4 \times 10^{-22} C^3 J^{-2}$. The average molecular second order electronic polarisability, SOEP[1.06], estimated from Khi$^{(2)}$, is $2.4 \times 10^{-49} C^3 J^{-2} m^3$ or $6.5 \times 10^{-29}$ cm$^5$/esu.

EXAMPLE 6

The procedure of Example 5 was repeated using OA2 (from Example 4) in place of OA1. The calculated value of the second order NLO coefficient, Khi$^{(2)}$, was $6.3 \times 10^{-22} C^3 J^{-2}$ and the average molecular second order electronic polarisability, SOEP[1.06] derived from Khi$^{(2)}$ is $1.97 \times 10^{-49} C^3 J^{-2} m^3$ or $5.3 \times 10^{-29}$ cm$^5$/esu.

We claim:

1. An azo compound of the formula:

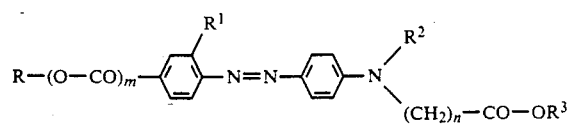

wherein

R is a non-hydrophilic aliphatic or cycloaliphatic group containing from 8 to 40 carbon atoms;

m is 0 or 1;

R$^1$ is NO$_2$, CN or COOR$^2$;

R$^2$ is H or C$_{1-4}$-alkyl;

n is from 1 to 4 and

R$^3$ is H, a metal or a group containing a tetravalent N atom wherein the N atom is attached directly to the O atom.

2. A compound according to claim 1 in which R is a group containing from 8 to 20 carbon atoms consisting of an unsubstituted alkyl, alkenyl or cycloalkyl group or such group interrupted by one oxygen or sulphur atom for every twelve carbon atoms, or substituted by halogen.

3. A compound according to claim 1 in which R is $C_{12-18}$-alkyl and $R^1$ is nitro.

4. A compound according to claim 1 in which $R^2$ is H, methyl or ethyl.

5. A compound according to claim 1 in which n is 1 or 2 and $R^3$ is H, cadmium, barium, lead or calcium.

6. The compound 4-(2-nitro-4-heptadecyloxycarbonylphenylazo)-N-methyl-N-(2-[hydroxycarbonyl]ethyl)aniline.

7. The compound 4-(2-nitro-4-dodecylphenylazo)-N-methyl-N-(2-[hydroxycarbonyl]ethyl)aniline.

* * * * *